United States Patent [19]
Hickman, Jr. et al.

[11] Patent Number: 5,402,066
[45] Date of Patent: Mar. 28, 1995

[54] METHOD AND APPARATUS FOR MAGNETICALLY TESTING ELONGATE OBJECTS USING TWO CIRCUMFERENTIALLY DISPOSED ARRAYS OF MAGNETS AND TWO CIRCUMFERENTIALLY DISPOSED ARRAYS OF SENSORS

[75] Inventors: William Hickman, Jr., Metairie; Joseph P. Dyer, Bossier City, both of La.

[73] Assignee: Commerical Technologies, Inc., Metairie, La.

[21] Appl. No.: 856,545

[22] Filed: Mar. 24, 1992

[51] Int. Cl.⁶ .................... G01N 27/82; G01R 33/12
[52] U.S. Cl. .................... 324/242; 324/232; 324/262
[58] Field of Search ............ 324/240, 241, 242, 243, 324/219, 220, 221, 232

[56] References Cited

U.S. PATENT DOCUMENTS

| | | | |
|---|---|---|---|
| 2,194,229 | 3/1940 | Johnston et al. | 324/232 |
| 2,882,488 | 4/1959 | Price et al. | 324/242 |
| 4,659,991 | 4/1987 | Weischedel. | |
| 4,827,215 | 5/1989 | Van Der Walt. | |
| 4,864,233 | 9/1989 | Harrison | 324/232 |
| 4,929,897 | 5/1990 | Van Der Walt. | |

FOREIGN PATENT DOCUMENTS 45862 8/1986 Poland.

OTHER PUBLICATIONS

Weischedel and Ramsey, Electromagnetic testing, a reliable method for the inspection of wire ropes in service, *NDT International* vol. 22 No. 3 Jun. 1989 (pp. 155–158).

PS Prosyst BV, Radio Telemetry Load Measuring Equipment, Product Description page, Nov. 1990.

*Primary Examiner*—Walter E. Snow
*Attorney, Agent, or Firm*—Haynes and Boone

[57] ABSTRACT

A magnetic interferometer for performing nondestructive magnetic induction testing and inspection of wire rope and cable. The device concentrically surrounds a wire rope or cable to be tested and includes means for inducing a magnetic field in the rope or cable as well as means for detecting flux changes in the induced magnetic field. By detecting flux changes in the magnetic field the condition of the rope or cable can be determined.

54 Claims, 10 Drawing Sheets

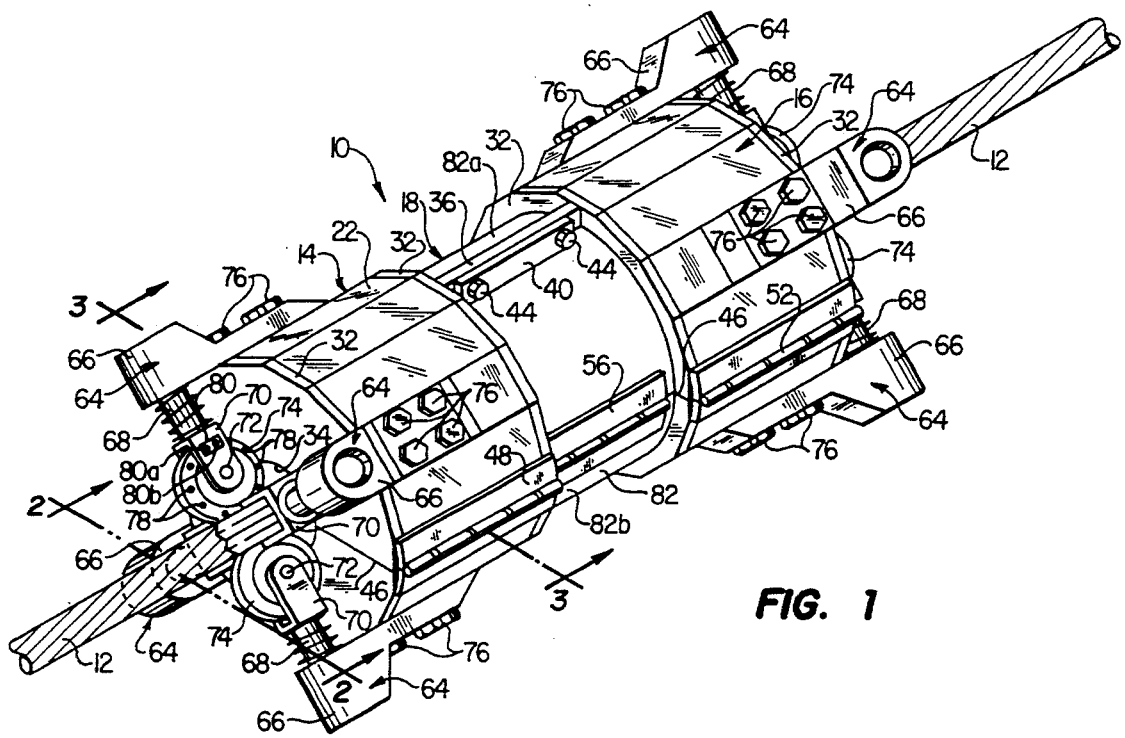
FIG. 1
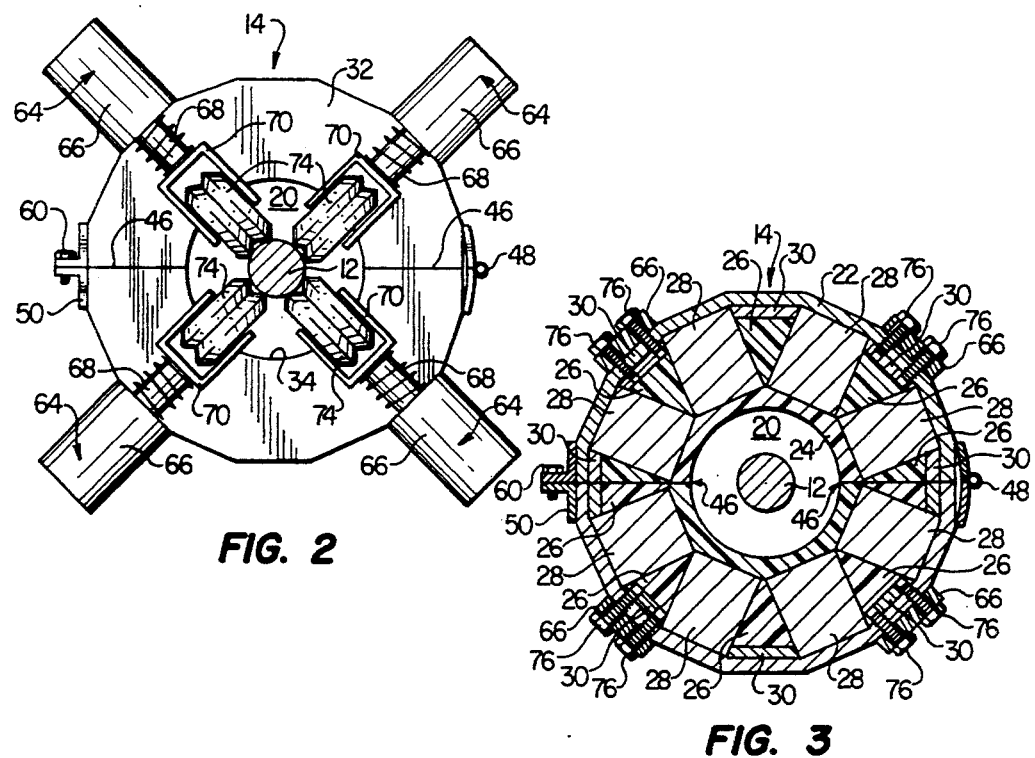
FIG. 2
FIG. 3

G311O2 AND APPARATUS FOR MAGNETICALLY TESTING ELONGATE OBJECTS USING TWO CIRCUMFERENTIALLY DISPOSED ARRAYS OF MAGNETS AND TWO CIRCUMFERENTIALLY DISPOSED ARRAYS OF SENSORS

BACKGROUND OF THE INVENTION

1. Field of the Invention

The present invention relates to a device for the inspection and quality control of wire rope and cables. The device is adapted to concentrically surround a portion of a wire rope or cable to be tested. The device induces a magnetic field in the wire rope or cable and senses any deviation in the magnetic field indicating an anomaly in the wire rope or cable.

2. Description of the Prior Art

Polish Patent No. 45,862 discloses an induction sensor of a measuring head for the inspection of cables. The induction sensor has a two-part frame with cutouts of different diameter in which are located two bifilar coils connected in series and arranged concentrically with respect to the axis of the sensor and separately in the upper and lower parts of the frame.

Polish Patent No. 122,500 discloses two devices for the inspection and quality control of steel cables. According to each device a cable is magnetized by a magnetic field set up by a circuit which includes permanent magnets, the steel cable and pole pieces which are attached to the permanent magnets and include sliding guides which contact the steel cable.

The devices disclosed in Polish Patent No. 122,500 have several serious drawbacks. First, the inclusion of the pole pieces and sliding guides, some of which are necessarily made of ferrous material, makes the devices quite large and quite heavy. In addition, due to the large size of these devices, they require that the cable undergoing testing be contacted by the sliding guides which are subject to failure due to frictional erosion after a certain period of use.

SUMMARY OF THE INVENTION

The magnetic interferometer of the present invention avoids the above-mentioned disadvantages which are characteristic of the prior art. The magnetic interferometer of the present invention provides a means for performing nondestructive magnetic induction testing and inspection of wire rope and cable.

The magnetic interferometer of the present invention is adapted to concentrically surround a wire rope or cable to be tested and comprises means for inducing a magnetic field in wire rope or cable and means for detecting flux changes in the induced magnetic field. A change in the flux of the induced magnetic field indicates that there is an anomaly in the cross-sectional profile of the wire rope or cable undergoing testing.

In a preferred embodiment of the present invention, the means for inducing a magnetic field comprises a pair of magnet housings, each of which is provided with a plurality of rectangular permanent magnets arranged to form a segmented cylinder spaced apart from and surrounding the wire rope or cable. Corresponding magnets of each housing are paired in alignment longitudinally to create a magnetic circuit having lines of magnetic flux passing axially through and parallel to the wire rope or cable.

In this preferred embodiment, the means for detecting flux changes in the induced magnetic field comprises a sensing device which includes longitudinally spaced inner and outer sensing arrays, each of which includes sensing elements circumscribing the wire rope or cable which are positioned perpendicular to the axis of the wire rope or cable. The elements are spaced apart from the wire rope or cable with the elements of the inner sensing array positioned closer to the wire rope or cable than the elements of the outer sensing array. The elements of the inner sensing array are aligned to be in the same longitudinal planes as corresponding magnet pairs. The elements of the outer sensing array are rotationally displaced relative to the inner sensing array so as to be aligned in longitudinal planes midway between corresponding magnet pairs. Bifilar, helical windings encircle each of the elements. The windings for each of the inner and outer arrays are connected respectively in series. An electromotive force is induced in the windings in response to magnetic flux changes in proximity thereto thus producing a signal which may be processed and which is indicative of the condition of the wire rope or cable.

BRIEF DESCRIPTION OF THE DRAWINGS

In describing the invention, reference will be made to the accompanying drawings, in which:

FIG. 1 is a perspective view of the magnetic interferometer of the present invention;

FIG. 2 is a section taken along the line 2—2 of FIG. 1;

FIG. 3 is a section taken along the line 3—3 of FIG. 1;

DETAILED DESCRIPTION OF THE PREFERRED EMBODIMENTS

Figure 4:
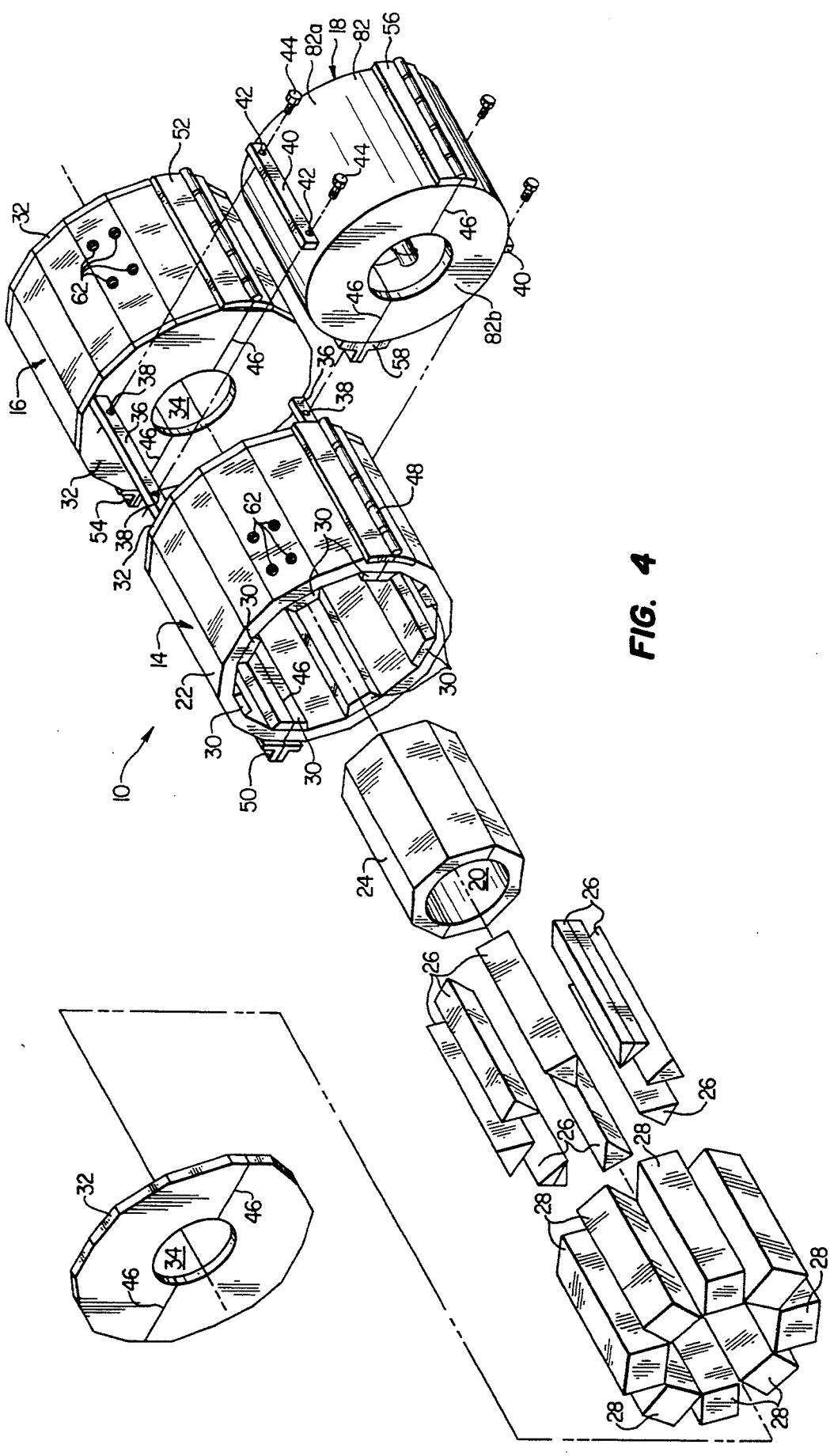
FIG. 4 is an exploded view of the magnetic interferometer shown in FIG. 1 with portions omitted for clarity.

Referring now to the drawings, and in particular to FIG. 1, a preferred embodiment of the magnetic interferometer of the present invention is generally indicated at 10. The magnetic interferometer 10 is adapted to concentrically surround a ferromagnetic metal wire rope or cable 12 to be tested for anomalies in its cross-sectional profile. As used herein, the term cable shall refer to any type of rope, wire, pipe, tubing, cable, or the like, made of ferromagnetic material.

The magnetic interferometer 10 includes a first magnet housing 14, a second magnet housing 16 and a sensing device 18 disposed between the first magnet housing 14 and the second magnet housing 16. The cable 12 is centrally located within a central bore 20 (see FIGS. 2 and 3) which runs the entire length of the magnetic interferometer 10 from the first magnet housing 14, through the sensing device 18, and through the second magnet housing 16.

In one embodiment of the present invention, and referring also to FIG. 4, the first magnet housing 14 includes an outer housing 22. The outer housing 22 is a sixteen-sided cylindrical member having a central cavity. It will be recognized by those skilled in the art that the outer housing 22 is not required to have sixteen sides, but may have any even number of sides greater than four, or as described below, the outer housing 22 may be cylindrical. In one embodiment of the present invention, the outer housing 22 comprises a magnetic conducting material such as steel, while in another embodiment, the outer housing 22 comprises a nonmagnetic material such as plastic for reasons to be described.

An inner housing 24 is concentrically disposed within the outer housing 22. The outer diameter of the inner housing 24 preferably has half as many sides as the outer housing 22. A plurality of spacers 26 are located between the inner housing 24 and the outer housing 22. Preferably, there is an equal number of spacers 26 as the number of sides of the outer diameter of the inner housing 24. Also, it is preferred that the number of spacers 26 is equal to one-half of the number of sides of the outer housing 22.

A plurality of permanent magnets 28 are also located between the inner housing 24 and the outer housing 22 and are arranged to form a segmented cylinder spaced apart from and surrounding the cable 12 with all of the magnets 28 being disposed such that the same pole of each of the magnets 28 is facing inward toward the cable 12. The number of magnets 28 is equal to the number of spacers 26.

As shown in FIG. 4, the inner diameter of the outer housing 22 includes a plurality of dividers 30. The number of dividers 30 is equal to the number of magnets 28. The magnets 28 are disposed between the inner housing 24 and the outer housing 22 adjacent respective dividers 30. The spacers 26 are located adjacent respective magnets 28 and between the inner housing 24 and the outer housing 22.

In one embodiment of the present invention, the spacers 26 comprise a plastic resin, such as fiberglass, which binds to adjacent magnets 28. In this embodiment, the inner housing 24 may be removed once the plastic resin hardens. In another embodiment of the present invention, the spacers 26 comprise an inert material which does not bind to the magnets 28, thus necessitating the presence of the inner housing 24 to maintain the magnets 28 within the first and second magnet housings 14 and 16, respectively. In still another embodiment, the spacers 26 are removed once the magnets 28 are in place, and the voids between the magnets 28 are filled with a nonmagnetically conducting material to maintain the magnets 28 within the first and second magnet housings 14 and 16, respectively.

The inner housing 24, the plurality of spacers 26 and the plurality of magnets 28 are maintained within the outer housing 22 by a pair of end caps 32 located at each end of the outer housing 22. The end caps 32 include a central cavity 34 which aligns with the central bore 20.

Although not shown in the drawings, the second magnet housing 16 includes an identical number and arrangement of the inner housing 24, the spacers 26, the magnets 28, the dividers 30 and the end caps 32, it being understood that the magnets 28 within the second magnet housing 16 are also disposed such that the same pole of each of the magnets 28 is facing inward toward the cable 12, that pole however being the opposite pole as the pole facing inward within the first magnet housing 14.

The first magnet housing 14 and the second magnet housing 16 are connected by a pair of diametrically opposed brackets 36. Each bracket 36 includes two threaded bores 38. Similarly, the sensing device 18 includes a pair of diametrically opposed flanges 40 which include a pair of threaded bores 42. The threaded bores 42 align with the respective threaded bores 38 of the brackets 36. The threaded bores 38 and 40 are adapted to threadingly engage bolts 44. In this manner, the sensing device 18 may be demountably attached to the magnetic interferometer 10 between the first magnet housing 14 and the second magnet housing 16.

As partially shown in FIGS. 3 and 4, the outer housing 22, the inner housing 24, a pair of diametrically opposed spacers 26, and the end caps 32 of the first magnet housing 14 are split in half by means of a medial slit 46. In a similar manner, all corresponding parts in the second magnet housing 16 are split in half by a medial slit 46. Moreover, the sensing device 18 is split in half by a medial slit 46. The split halves of the first magnet housing 14 are maintained in facing relationship by a hinge 48 and a bracket assembly 50. In a similar manner, the split halves of the second magnet housing 16 are maintained in facing relationship by a hinge 52 and a bracket assembly 54. Finally, the split halves of the sensing device 18 are maintained in facing relationship by a hinge 56 and a bracket assembly 58. The bracket assembly 50 on the first magnet housing 14 is divided into two identical halves by a medial slit 46. The two halves of the bracket assembly 50 are maintained in facing relationship by a bolt 60. In a similar manner, the bracket assembly 54 of the second magnet housing 16 and the bracket assembly 58 of the sensing device 18 are divided into equal halves by a medial slit 46, as shown in FIG. 4, and are maintained in facing relationship by a similar bolt (not illustrated).

The outer housing 22 of the first magnet housing 14 and the outer housing 22 of the second magnet housing 16 each include a respective set of four threaded bores 62. Although not shown in the drawings, the outer housing 22 of the first magnet housing 14 and the outer housing 22 of the second magnet housing 16 each include three additional sets of four threaded bores 62; one set being located diametrically opposite the illustrated set of bores 62, and the other two sets of bores 62 being diametrically opposed and disposed along an axis that is perpendicular to an axis formed by the illustrated set of bores 62 and the diametrically opposed set of bores 62. The purpose of the threaded bores 62 will be discussed below.

Referring to FIGS. 1 and 2, the first magnet housing 14 includes two pairs of diametrically opposed roller guide assemblies 64 in which the axis between one set of diametrically opposed roller guide assemblies 64 is perpendicular to the axis between the other set of diametrically opposed roller guide assemblies 64. The second magnet housing 16 includes a complementary set of two pairs of diametrically opposed roller guide assemblies 64 (shown partially in FIG. 1). Each of the roller guide assemblies 64 includes a housing 66 and a spring-loaded shaft 68. One end of each spring-loaded shaft 68 communicates with the housing 66 and the other end of each spring-loaded shaft 68 is connected to a roller bracket 70. Each roller bracket 70 retains an axle 72 with a roller guide 74 mounted on each axle 72, it being understood that the size of the roller guides 74 can be varied to accommodate different sizes of cables 12.

As discussed above, the first magnet housing 14 and the second magnet housing 16 include two sets of four diametrically opposed threaded bores 62. The roller guide assemblies 64 are mounted to the first magnet housing 14 and the second magnet housing 16 by threaded bolts 76 that engage with the threaded bores 62. In an alternate embodiment, the first magnet housing 14 and the second magnet housing 16 include only one pair of diametrically opposed roller guide assemblies 64.

As shown on FIG. 1, the magnetic interferometer 10 preferably includes a plurality of magnets 78 disposed within one of the roller guides 74 in a circumferential pattern. The magnets 78 are inserted into the roller guide 74 such that their magnetic poles alternate about the circumference. The alternating magnetic poles have an associated alternating magnetic flux which is detected in the magnetic interferometer 10 by a speed and location sensor 80. The speed and location sensor 80 includes two Hall effect switches 80a and 80b for detecting each time one of the magnets 78 passes by the speed and location sensor 80. The magnets 78 are preferably spaced such that one of the magnets 78 passes by the speed and location sensor 80 for every inch the magnetic interferometer 10 travels along the cable 12. The Hall effect switch 80a provides a digital signal as alternating poles of the magnets 78 pass by it yielding an identification of how far the magnetic interferometer 10 has traveled along the cable 12. The Hall effect switch 80b provides an identification of any changes in direction of the magnetic interferometer 10 by detecting any two successive identical magnetic fluxes resulting from the successive passage of the same magnet 78.

Figure 5:
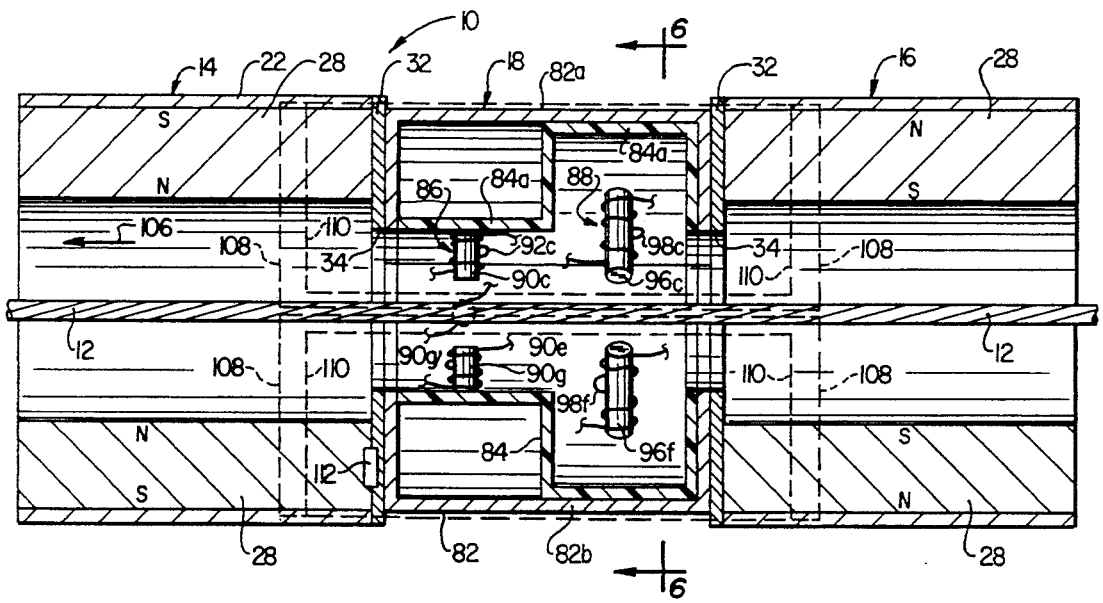
FIG. 5 is a longitudinal section of the magnetic interferometer of the present invention with portions omitted for clarity.
Figure 6:
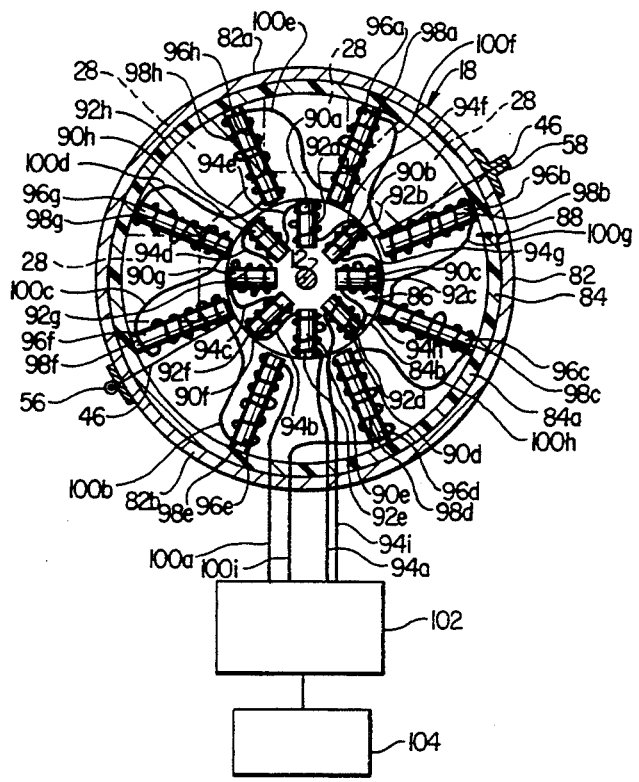
FIG. 6 is a section taken along line 6—6 of FIG. 5.

Referring to FIGS. 5 and 6, the sensing device 18 includes a housing 82, a cylinder 84 disposed within the housing 82, and first and second sensing arrays designated respectively by the reference numerals 86 and 88. The housing 82 is divided into upper and lower portions 82a and 82b which are connected by the hinge 56 and the bracket 58, previously described. The cylinder 84 includes a large diameter portion 84a and a reduced diameter portion 84b for housing the second and first sensing arrays 88 and 86, respectively. Although not shown, it is understood that the cylinder 84 may be divided into two portions in a manner similar to the housing 82. It is understood that the housing 82 is constructed of either a magnetically conductive or nonconductive material and the cylinder 84 is constructed of plastic or a similar magnetically nonconductive material.

Eight sensing elements 90a–90h having helical wire windings 92a–92h, respectively, comprise the first sensing array 86. The elements 90a–90h are connected by fasteners (not shown) to the inner wall of the reduced diameter portion 84b. Windings 92a–92h are connected electrically in series by wires 94a–94i, as shown.

Eight sensing elements 96a–96h having helical wire windings 98a–98h, respectively, comprise the second sensing array 88. The elements 96a–96h are connected by fasteners (not shown) to the inner wall of the large diameter portion 84a. Windings 98a–98h are connected electrically in series by wires 100a–100i, as shown.

The first and second sensing arrays 86 and 88 are connected by the respective wires 94a, 94i and 100a, 100i to a digital signal processor 102 and a microcontroller 104, as will be discussed.

The elements 90a–90h and 96a–96h are configured as rods constructed of a ferromagnetic material and are positioned perpendicular to the axis of and radially spaced around the cable 12 undergoing testing. The ends of the elements 90a–90h and 96a–96h are spaced apart from the cable 12 such that the only direct contact of the magnetic interferometer 10 with the cable 12 is by the roller guides 74. The elements 90a–90h are positioned closer to the cable 12 than the elements 96a–96h, for reasons subsequently discussed.

The elements 90a–90h of the first sensing array 86 are aligned in longitudinal planes which are the same for corresponding pairs of the magnets 28, so that each of the elements and corresponding magnet pairs share the same radial center line from the cable 12, as depicted in FIG. 6. The elements 96a–96h of the second sensing array 88 occupy different longitudinal planes than the elements 90a–90h of the first sensing array 86 for reasons subsequently discussed. The elements 96a–96h are aligned in longitudinal planes which are midway between the longitudinal planes of corresponding pairs of the magnets 28, and the adjacent magnets 28, as shown in FIG. 6, it being understood that alignment of the elements 90a–90h and 96a–96h could be reversed.

The windings 92a–92h and 98a–98h are wound in order to allow a voltage to be induced through the windings as a result of the relative motion of the cable 12 as indicated by an arrow 106 producing perturbations in magnetic flux lines 108 and 110, as will be discussed. The windings can either be continuously wound or bifilar wound, with bifilar windings resulting in increased amplitudes of the induced voltages.

Besides the speed and location sensor 80 and the first and second sensing arrays 86 and 88, a Hall effect sensor 112 is also disposed within the magnetic interferometer 10 to detect the presence of magnetic flux for reasons discussed below. Preferably and as shown on FIG. 5, the Hall effect sensor 112 is disposed within the first magnet housing 14 between one of the magnets 28 and the inner end cap 32.

Figure 7:
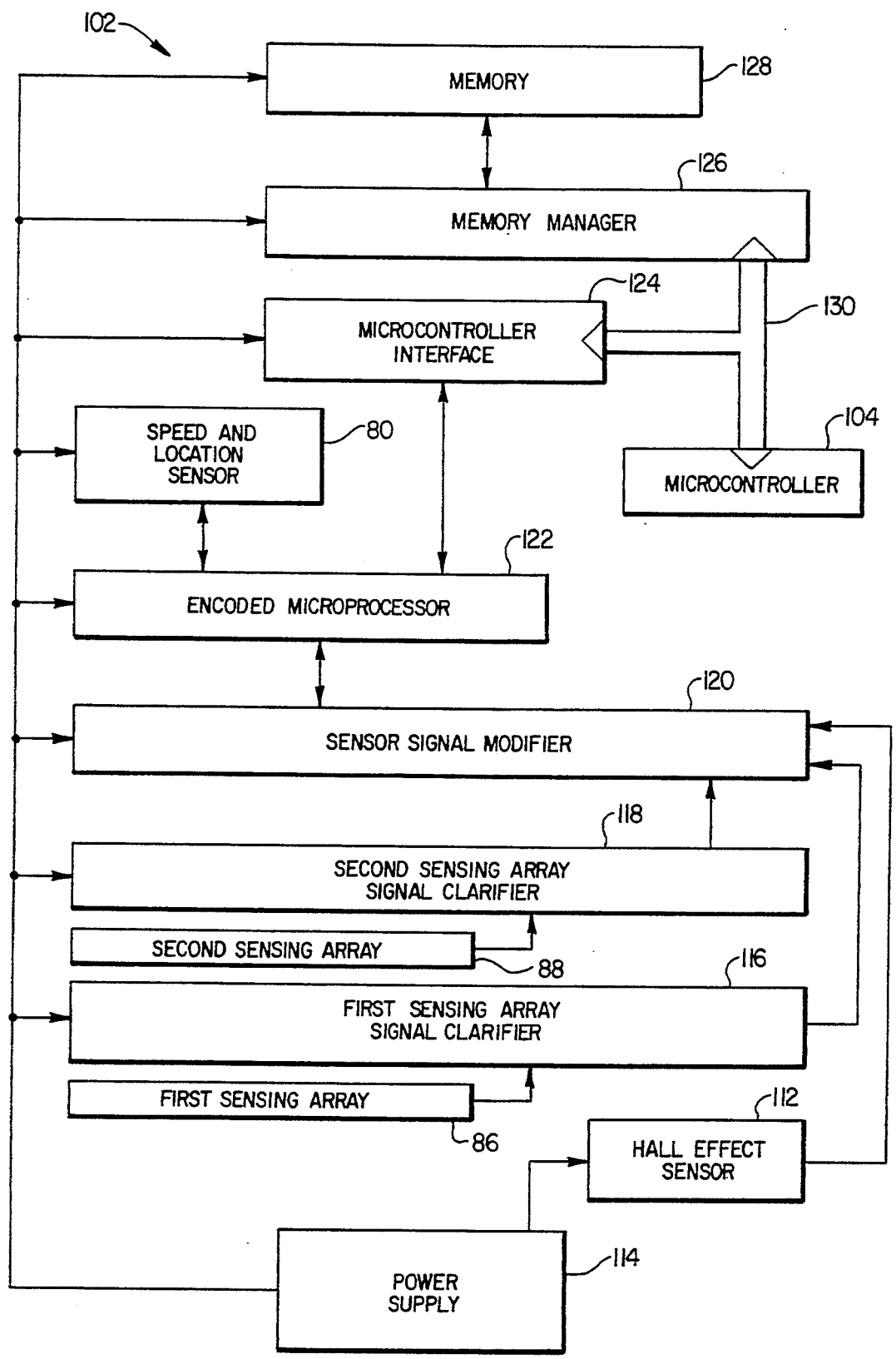
FIG. 7 is a functional block diagram of the digital signal processor of the present invention.

Referring to FIG. 7, a functional block diagram of the digital signal processor 102 of the present invention is shown which takes data from the first sensing array 86, the second sensing array 88, the speed and location sensor 80 and the Hall effect sensor 112, filters and processes the data as required, and stores the data in memory for later retrieval and subsequent processing by the microcontroller 104. The processor 102 includes a power supply 114, a first sensing array signal clarifier 116, a second sensing array signal clarifier 118, a sensor signal modifier 120, an encoded microprocessor 122, a microcontroller interface 124, a memory manager 126 and a memory 128. The processor 102 is preferably integral with the exterior of the magnetic interferometer 10 to allow autonomous data collection. A RS 232 serial port 130 is provided for connecting the processor 102 to the microcontroller 104 to process the data. As the microcontroller 104 is conventional, it will not be described in any further detail.

In use, the bolt 60 of the first magnet housing 14 is removed and the corresponding bolts are removed from the bracket assembly 54 of the second magnet housing 16 and the bracket assembly 58 of the sensing device 18. The first magnet housing 14, the second magnet housing 16, and the sensing device 18, including their respective internal parts, are opened by means of the respective hinges 48, 52 and 56, and the magnetic interferometer 10 is positioned and closed to concentrically surround a portion of the cable 12 to be tested.

As shown most clearly in FIGS. 1 and 2, the cable 12 is engaged by the diametrically opposed roller guides 74 at respective ends of the magnetic interferometer 10. By means of the spring loaded shafts 68 which urge the roller guides 74 to extend from and allow the roller guides 74 to contract within the housing 66, the magnetic interferometer 10 can accommodate a wide variety of cables having different diameters. Also, by means of the roller guides 74, the cable 12 is centrally located within the central bore 20 as previously discussed.

The magnets 28 disposed within the first magnet housing 14 and the second magnet housing 16 set up a magnetic flux pattern, discussed below, that is detected by the sensing device 18. When the magnetic interferometer 10 and the cable 12 are moved relative to each other in a conventional manner as indicated by the arrow 106 in FIG. 5, any deviation in the cross-sectional thickness of the cable 12 causes a perturbation in the magnetic flux lines 108 and 110 set up by the plurality of magnets 28 and this perturbation is detected by the sensing device 18.

When the outer housings 22 of the first and second magnet housings 14 and 16 are magnetic conductors, the magnetic circuit is established across the outer housings 22 and is completed by the cable 12. When the outer housings 22 and the housing 82 are made of a plastic material, they form no part of the magnetic circuit and the magnetic circuit is established between aligned sets of magnets 28 and is completed by the cable 12. When the housings 22 and 82 are made of a magnetically nonconductive material, the magnetic circuit is more highly concentrated in the cable 12, thereby increasing the signal amplitude generated by a flaw in the cable 12, as is discussed below.

As shown in FIG. 5, a leakage flux is established in the air space around the cable 12 as represented by the magnetic flux line 110. If the magnetic cross-section of the cable 12 is constant and the structural integrity of the cable 12 is uniform, then the magnetic flux line 110 representing the leakage flux and the magnetic flux within the cable 12, represented by magnetic flux line 108, run parallel to the axis of the cable 12. In the case of abrupt changes (hereinafter "defects") in the magnetic cross-sectional area of the cable 12 caused by, among other things, breaks, corrosive pits, loops or corkscrews, the magnetic flux within and surrounding the cable 12 is perturbed and the magnetic flux lines 108 and 110 are deflected. These perturbations or changes in the magnetic flux result in a voltage being induced in both of the first and second sensing arrays 86 and 88, the amplitude of which depends upon the location and magnitude of the magnetic flux change. The signal value of the induced voltage depends upon the size and type of the defect and is proportional to the local change of the magnetic cross-sectional area of the cable 12.

The Hall effect sensor 112 is provided to detect gradual changes in the magnetic cross-sectional area of the cable 12, caused by, among other things, stretching, erosion and wear, which cause deviations in the magnetic flux lines 108 and 110 within and surrounding the cable 12. These reductions or gradual changes in the magnetic flux result in a change in the voltage being induced in the Hall effect sensor 112. The relative size of the voltage change induced in the Hall effect sensor 112 is directly proportional to the local change of the magnetic cross-sectional area of the cable 12 and can be used for the automatic gain control of the signals produced by both the first and second sensing arrays 86 and 88 and for determining the amount of wear and stretching of the cable 12.

It is understood that each element 90a–90h and 96a–96h of the first and second sensing arrays 86 and 88 will detect a given defect in the cable 12, however a particular defect will be more strongly detected by the particular element or elements which are closest in radial proximity to the location of the defect. Since the elements 90a–90h occupy longitudinal planes which are rotationally displaced relative to the elements 96a–96h, the signals produced by the first and second sensing arrays 86 and 88, respectively, will be different according to the radial location of the defect in the cable 12. The placement of the elements 90a–90h of the first sensing array 86 closer to the cable 12 will increase the ability to detect subsurface defects within the cable 12 and further differentiate the signals produced by the first and second sensing arrays 86 and 88, respectively. The respective placement of the elements 90a–90h and 96a–96h thereby allows the precise nature and location of a defect within the cable 12 to be determined due to the different effects each defect will have on each element. Since the first and second sensing arrays 86 and 88 are longitudinal displaced, it is understood that one of the arrays will detect a defect prior to the other, depending on the direction of movement of the cable 12 relative to the sensing device 18.

As shown in FIG. 7, the Hall effect sensor 112 transmits a signal voltage proportional to the magnetic field strength of the magnetic flux lines 108 and 110 to the sensor signal modifier 120. The signal from the Hall effect sensor 112 is used by the sensor signal modifier 120 to automatically adjust the voltage level of the signals received from the first and second sensing arrays 86 and 88, respectively. The first and second sensing array clarifiers 116 and 118 filter the adjusted first and second sensing array signals, respectively, and attenuate any noise outside the center frequencies of the clarifiers 116 and 118, preferably being 30 Hz and 100 Hz respectively, to provide the sensor signal modifier 120 with both filtered and unfiltered signals. The sensor signal modifier 120 then transforms the analog signals to digital signals and provides the encoded microprocessor 122 with a digital representation of the unfiltered first and second sensing array signals, the filtered first and second sensing array signals and the Hall effect sensor signal.

The encoded microprocessor 122 also receives the already digital data from the speed and location sensor 80. From this additional data, the encoded microprocessor 122 determines the present speed and location of the magnetic interferometer 10 and produces a data sample representing the signal from the first sensing array 86, the signal from the second sensing array 88, the signal from the Hall effect sensor 122, the sum of the signals from the first and second sensing arrays 86 and 88, the filtered signals from the first and second sensing arrays 86 and 88, and the speed and location of the magnetic interferometer 10. The memory manager 126 can then be used to either store the data sample in the memory 128 or transmit the data sample to the microcontroller 104, depending on whether the microcontroller 104 is connected to the processor 102.

In one mode of operation, the data samples are collected at a rate of 8 bytes per sample and at 8 samples per inch of cable and are stored in the on-board memory 128, thereby providing the magnetic interferometer 10 with the capacity to autonomously collect data. Subsequent to testing, the microcontroller 104 is connected to the processor 102 via the RS 232 serial port 130 so that the data samples can be transferred to the microcontroller 104 which then interprets the digital signals from the processor 102 in a manner to quantify the condition of the cable 12 and to determine the type and location of each defect in the cable 12. Alternately, the microcontroller 104 can be connected to the processor 102 during testing, thereby providing the magnetic interferometer 10 with the ability to produce real time output and the capacity to collect data samples from any length cable.

The encoded microprocessor 122 is encoded so as to prevent operator access to the microcoded software internal to the microprocessor 122. The microcontroller interface 124 is therefore provided to allow the system operator to communicate to the encoded microprocessor 122 and calibrate the magnetic interferometer 10, as will be described.

As mentioned above, the microcontroller 104 interprets the digital signals from the processor 102 in a manner to quantify the condition of the cable 12 and to determine the type and location of each defect in the cable 12. To this end, each of the signals from the first and second sensing arrays 86 and 88, the Hall effect sensor 112 and the speed and location sensor 80 may be transmitted to the microcontroller 104 individually and in combination to perform integration and differentiation operations between the signals. The individual, combined, integrated and differentiated signals may then be interpreted to obtain additional information concerning the nature of the defects in the cable 12.

Figure 8:
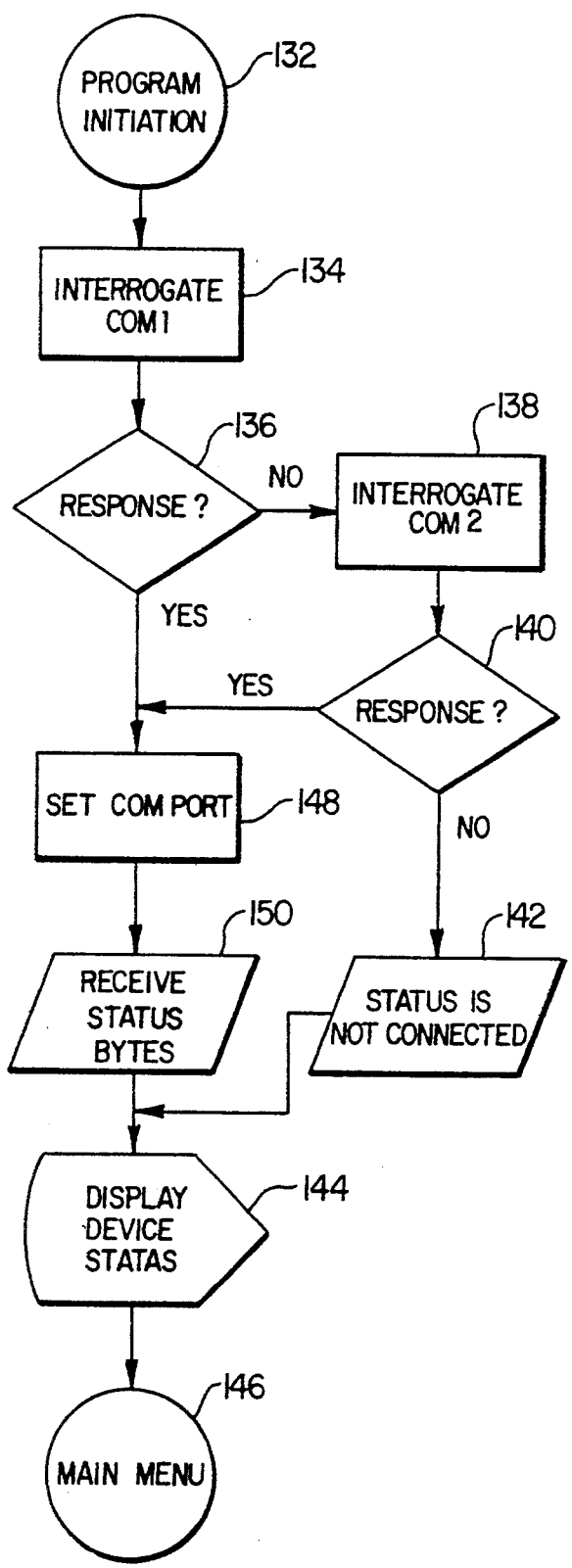
FIG. 8 is a flow chart illustrating the program logic for the initialization of the microcontroller.

FIG. 8 is a flow chart illustrating the initialization program logic. It is understood that the logic is implemented by computer instructions contained within the microcontroller 104. In block 132, the software operation begins with the program initialization. In block 134, the software attempts to interrogate the microprocessor 104 via communication line 1 and control is transferred to block 136. In block 136, the software waits a predetermined period of time to determine if the microcontroller 104 is connected to the processor 102 via communication line 1. If it is not so connected, control proceeds to block 138 where the software attempts to interrogate the microprocessor 104 via communication line 2 and control is transferred to block 140. In block 140, the software waits a predetermined period of time to determine if the microcontroller 104 is connected to the processor 102 via communication line 2. If it is not so connected, control proceeds to block 142 where the decision is made that the microcontroller 104 is not connected to the processor 102 and control is transferred to block 144. In block 144, the microcontroller 104 displays the current status that the microcontroller 104 is not connected to the processor 102, and control is returned to the main menu in block 146.

If communication is established by either communication line 1 or communication line 2 in blocks 136 or 140, respectively, then control proceeds to block 148 where the software establishes a communication link to provide the current status. Control then proceeds to block 150 where the microcontroller 104 receives the status of the processor 102. Control then proceeds to block 144 where the microcontroller 104 displays the current status of the processor 102 for a predetermined time. The program displays a current status that the processor 102 is idle, acquiring data, transferring data, or that data is available for transfer, and control is returned to the main menu in block 146.

Figure 9:
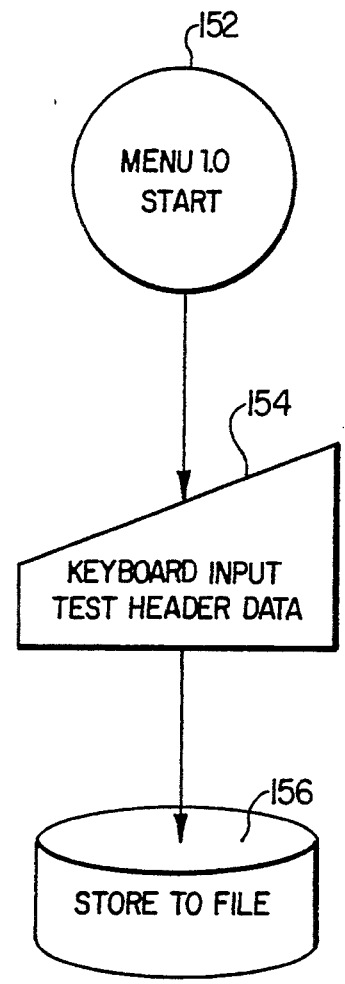
FIG. 9 is a flow chart illustrating the program logic for the initialization of the header file.

FIG. 9 is a flow chart illustrating the control logic for initialization of a header file. In block 152, the program begins by displaying the main menu and the operator selects option 1.0 to transfer control to block 154. In block 154, the operator provides the program with header information, such as, the operator's name, the test location, the time of the test and other data as may be desired. In block 156, the input header information is stored in a header file for subsequent display and/or print out.

Figure 10:
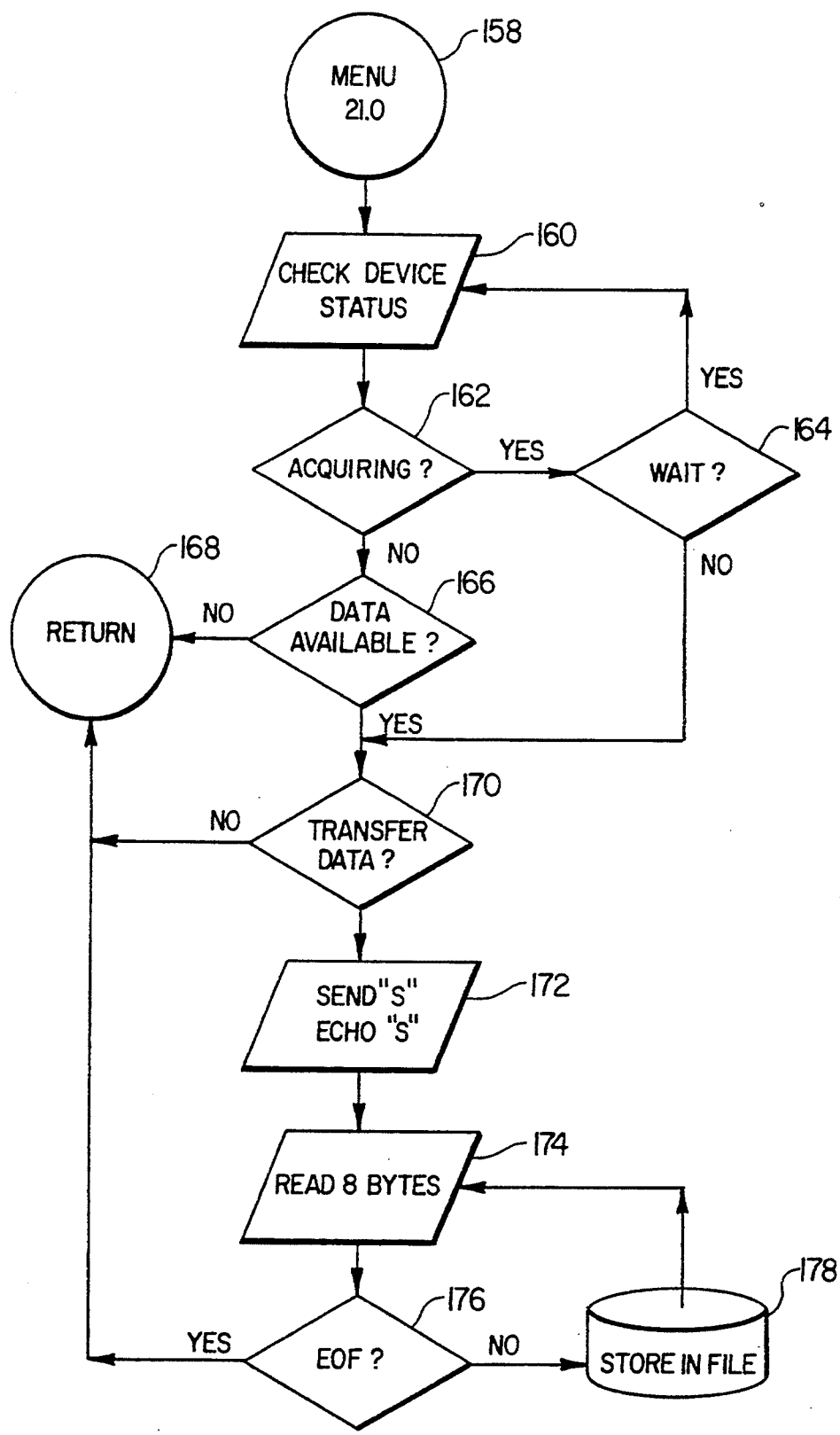
FIG. 10 is a flow chart illustrating the program logic for the acquisition and transfer of data.

FIG. 10 is a flow chart illustrating the program logic for the acquisition and transfer of data. In block 158, the program begins with the operator selecting option 2.1.0 from the main menu which transfers control to block 160. In block 160, the program determines the current status of the magnetic interferometer 10 which is idle, acquiring data, transferring data or has data available for transfer, and then displays the current status to the operator. Control is then transferred to block 162 where the decision is made as to whether the magnetic interferometer 10 is acquiring data. If the magnetic interferometer 10 is acquiring data, then control is transferred to block 164. In block 164, the operator has the option of waiting until the magnetic interferometer 10 has completed acquiring data. If the operator desires to wait, then the program returns to block 160 until the status changes. If the operator decides in block 164 not to wait for completion of the data acquisition, then control is transferred to block 170.

If the magnetic interferometer 10 is not acquiring data, then control is transferred to block 166. In block 166, it is determined if the magnetic interferometer 10 has data available for transfer. If no data is available for transfer, then control is transferred to block 168, and the program returns to the main menu. If it is determined in block 166 that data is available for transfer, then, as when the operator decides in block 164 not to wait for completion of the data acquisition, control is transferred to block 170. In block 170, the operator is prompted as to whether data is to be transferred. If the operator does not desire for data to be transferred, then the control is transferred to block 168 and the program returns to the main menu. If the operator does desire for data to be transferred, then control is transferred to block 172. In block 172, a command instruction "S" is sent to the memory manager 126 and the magnetic interferometer 10 responds by echoing the command instruction back to the microcontroller 104. Control is then transferred to block 174.

In block 174, the microcontroller 104 reads the first data sample which consists of, as previously mentioned, 8 bytes of data, and control is transferred to block 176.

In block 176, the microcontroller 104 determines if the end of the data file has been reached. If the end of the data file has not been reached, then control is transferred to block 178. In block 178, the microcontroller 104 stores the data sample in memory and control is transferred back to block 174 to repeat the procedure. If in block 176 it is determined that the end of the data file has been reached, then control is transferred to block 168 and the program returns to the main menu.

Figure 11:
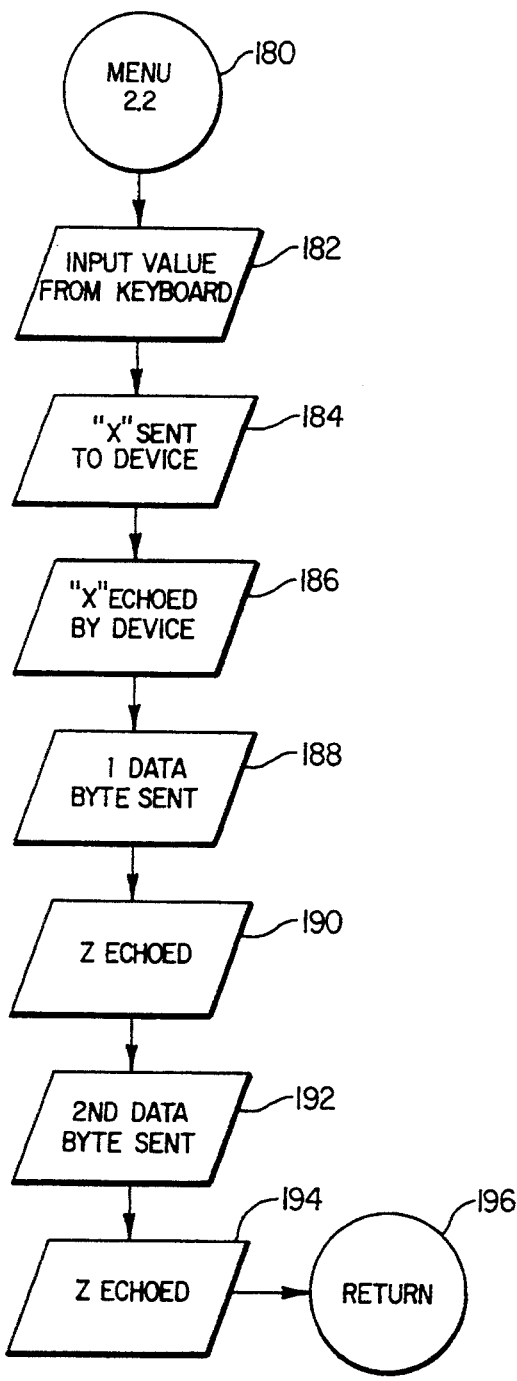
FIG. 11 is a flow chart illustrating the program logic for the calibration of the interferometer.

FIG. 11 is a flow chart illustrating the program logic for the calibration of the magnetic interferometer 10. In block 180, the program begins with the operator selecting option 2.2 from the main menu which transfers control to block 182. In block 182, the operator has the option of selecting a numeric value from 1 to 5 corresponding, respectively, to the voltage output range for the first sensing array 86, the voltage output range for the second sensing array 88, the analog to digital converter sensitivity for the first sensing array 86, the analog to digital converter sensitivity for the second sensing array 88 and a cable stop counter.

In block 184, the microcontroller 104 transmits the selected numeric value to the encoded microprocessor 122 via the microcontroller interface 124 and control is transferred to block 186. In block 186, the selected numeric value is echoed back to the microcontroller 104 and control is transferred to block 188. In block 188, the operator is prompted for the first calibration data byte, the data byte is transmitted to the encoded microprocessor 122, and control is transferred to block 190. In block 190, the encoded microprocessor 122 echoes the character "Z" back to the microcontroller 104 and control is transferred to block 192. In block 192, the operator is prompted for the second data byte which is then transmitted to the encoded microprocessor 122 and control is transferred to block 194. In block 194, the encoded microprocessor 122 echoes the character "Z" back to the microcontroller 104 and control is transferred to block 196. In block 196, control is returned to the main menu.

If in block 182 the operator of the microprocessor 104 had selected a numeric value of 1 corresponding to the selection of the voltage output range for the first sensing array 86, then the first and second data bytes would correspond to the positive and negative voltage output levels for the desired voltage output range for the first sensing array 86. If in block 182 the operator had selected a numeric value of 2 corresponding to the selection of the voltage output range for the second sensing array 88, then the first and second data bytes would correspond to the positive and negative levels for the desired voltage output range for the second sensing array 88. If in block 182 the operator had selected a numeric value of 3 corresponding to the selection of the analog to digital converter sensitivity for the first sensing array 86, then the first and second data bytes would correspond to the positive and negative voltage sensitivity levels for the two respective analog to digital converters for the first sensing array 86. If in block 182 the operator had selected a numeric value of 4 corresponding to the selection of the analog to digital converter sensitivity for the second sensing array 88, then the first and second data bytes would correspond to the positive and negative voltage sensitivity levels for the two respective analog to digital converters for the second sensing array 88. If in block 182 the operator had selected a numeric value of 5 corresponding to the selection of the cable stop counter, then the first and second data bytes would correspond to the length of the cable 12 to be measured and the period of time the magnetic interferometer 10 is to be operating.

Figure 12:
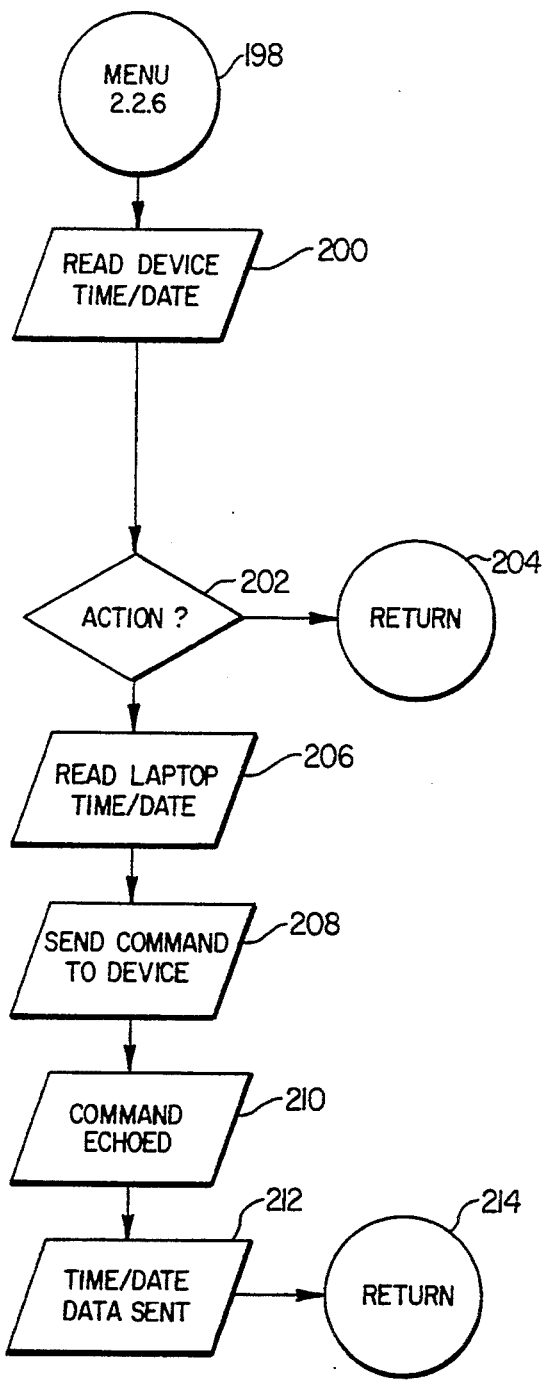
FIG. 12 is a flow chart illustrating the program logic for the interrogation and reset of the interferometer's internal clock.

FIG. 12 is a flow chart illustrating the program logic for the interrogation and reset of the internal clock/calendar of the magnetic interferometer 10. In block 198, the program begins with the operator selecting option 2.2.6 from the main menu and control is transferred to block 200. In block 200, the microcontroller 104 interrogates the internal clock/calendar, displays its current time and date, and then control is transferred to block 202. In block 202, the operator has the option to either reset the internal clock/calendar or accept the currently displayed time and date. If the operator decides that the currently displayed time and date are acceptable, then control is transferred to block 204 and the program returns to the main menu.

If the operator decides that the currently displayed time and date are not acceptable, then control is transferred to block 206. In block 206, the correct time and date are read from the microcontroller 104 and control is transferred to block 208. In block 208, a command signal is sent to the magnetic interferometer 10 to accept the new time and date, and control is transferred to block 210. In block 210, the program waits for the command to be echoed back from the magnetic interferometer 10, and when the command signal is returned, control is transferred to block 212. In block 212, the desired time and date are sent to the magnetic interferometer 10, and control is transferred to block 214 where the program returns to the main menu.

Figure 13:
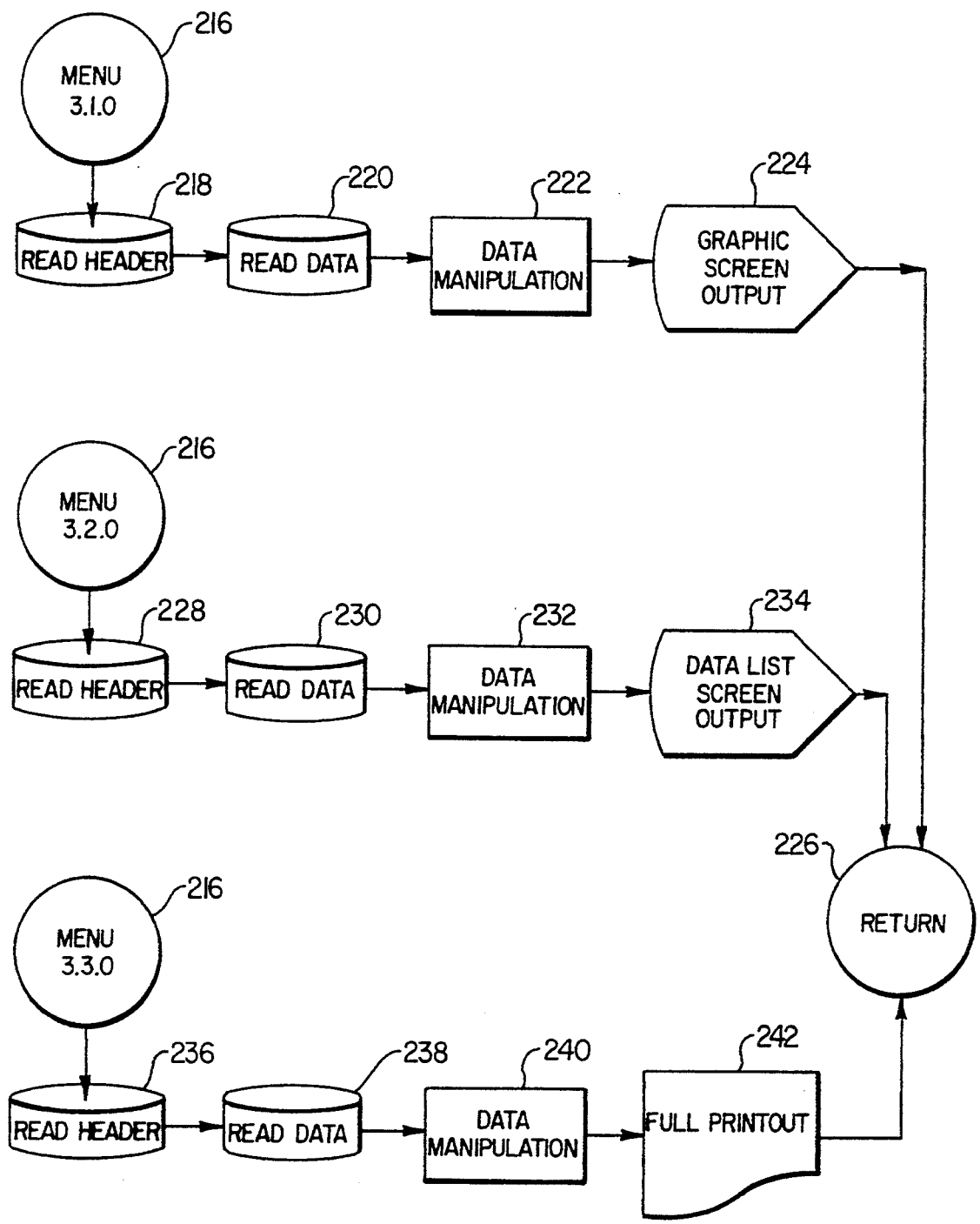
FIG. 13 is a flow chart illustrating the program logic to print and display the acquired data.

FIG. 13 is a flow chart illustrating the program logic to print and display the acquired data samples having options 3.1.0, 3.2.0 and 3.3.0 in the main menu in block 216. If the operator selects option 3.1.0 from the main menu, control is transferred to block 218. In block 218, the microcontroller 104 reads the header file and control is transferred to block 220. In block 220, the microcontroller 104 reads the data samples and control is transferred to block 222. In block 222, the microcontroller 104 evaluates the data samples, as previously described, and formats the results for graphical display and printout. Control is then transferred to block 224 in which the results are displayed and printed, and control is transferred to block 226 where the program returns to the main menu.

If in block 216, the operator selects option 3.2.0 from the main menu, then control is transferred to block 228. In block 228, the microcontroller 104 reads the header file and control is transferred to block 230. In block 230, the microcontroller 104 reads the data samples and control is transferred to block 232. In block 232, the microcontroller 104 evaluates the data samples, as previously described, and formats the results for numerical display, and control is transferred to block 234. In block 234, the results are displayed and printed, and control is transferred to block 226 where the program returns to the main menu.

If in block 216, the operator selects option 3.3.0 from the main menu, then control is transferred to block 236. In block 236, the microcontroller 104 reads the header file and control is transferred to block 238. In block 238, the microcontroller 104 reads the data samples and control is transferred to block 240. In block 240, the microcontroller 104 evaluates the data samples, as previously described, and formats the numerical results for both graphical and numerical display and printout, and control is transferred to block 242. In block 242, the results are displayed and printed, and control is transferred to block 226 where the program returns to the main menu.

Figure 14:
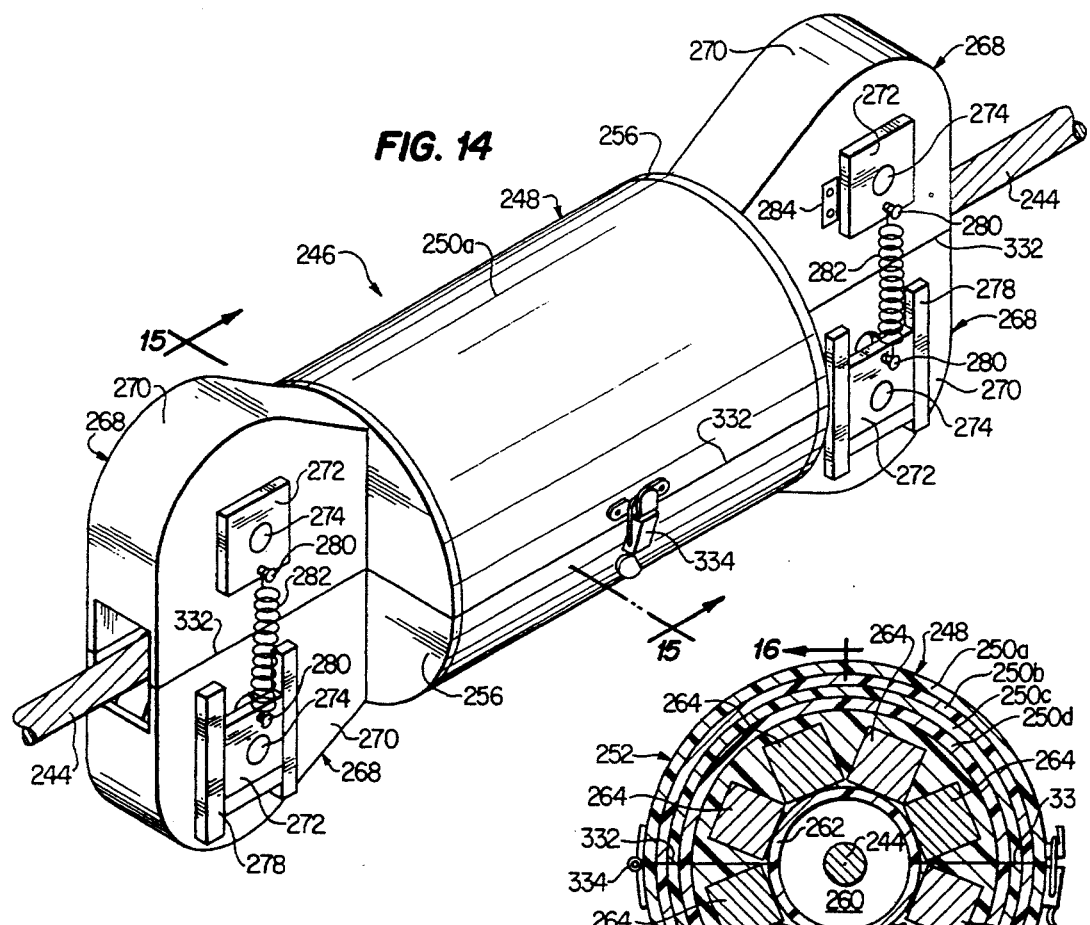
FIG. 14 is a perspective view of an alternative embodiment of the present invention.
Figure 15:
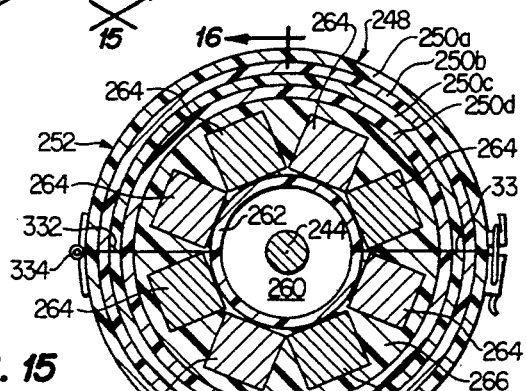
FIG. 15 is a section taken along the line 15—15 of FIG. 14.

FIGS. 14–17 show another embodiment of the present invention which also uses signals generated by perturbations in a magnetic flux generated through a cable 244 to detect structural anomalies in the cable 244. Referring specifically to FIG. 14, a magnetic interferometer 246 is shown which is adapted to concentrically surround the cable 244 to be tested for structural anomalies. The magnetic interferometer 246 includes an outer housing 248 which is comprised of a plurality of concentric, cylindrical plastic pipes 250a–250f which collectively enclose a first magnet housing 252, a second magnet housing 254, both of which have end caps 256 located at each of their respective ends, and a sensing device 258 disposed between the first magnet housing 252 and the second magnet housing 254. The cable 244 is centrally located within a central bore 260 (see FIGS. 15–17) which runs the entire length of the magnetic interferometer 246 from the first magnet housing 252, through the sensing device 258, and through the second magnet housing 254.

In this embodiment of the present invention, the outermost pipe 250a extends over and between the two outermost end caps 256 of the interferometer 246. The pipes 250b and 250c, like the pipe 250a, also extend between the two outermost end caps 256, but they abut the interior walls of the outermost end caps 256, respectively. The pipe 250d only encloses the first magnet housing 252, the pipe 250e only encloses the second magnet housing 254, and the pipe 250f only encloses the sensing device 258, as will be described.

Concentrically disposed within each of the pipes 250d and 250e, respectively, is an inner housing 262 of non-magnetically conducting material which, preferably, is a cylindrical plastic sleeve. A plurality of permanent magnets 264 are disposed between the pipes 250d and 250e and the inner housings 262, respectively, and are arranged to form segmented cylinders spaced apart from and surrounding the cable 244 with all of the magnets 264 being disposed such that the same pole of each of the magnets 264 is facing inward toward the cable 244, it being understood that the magnets 264 within the second magnet housing 254 have the opposite pole facing inward toward the cable 244 than the pole facing inward within the first magnet housing 252.

Once the magnets 264 are positioned, the voids between the magnets 264 are filled with a nonmagnetically conducting material 266 to maintain the magnets 264 within the first and second magnet housings 252 and 254, respectively.

It should be understood that although the pipes 250a–250e, the inner housing 262 and the material 266 have all been described as separate elements, they could all be formed as a single element, such as by plastic injection molding.

Figure 16:
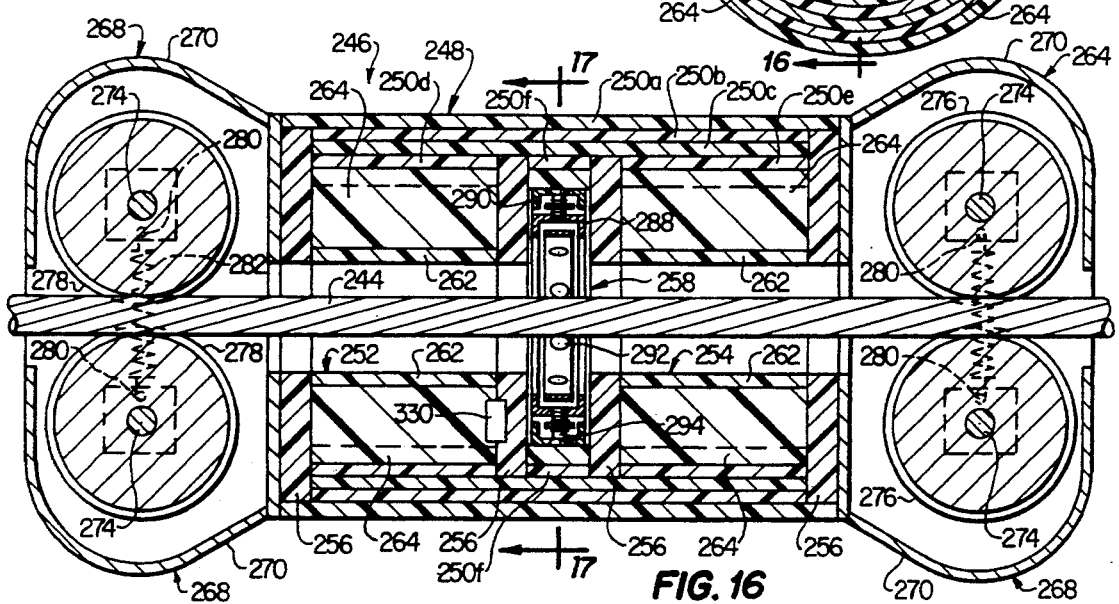
FIG. 16 is a section taken along the line 16—16 of FIG. 15.

Referring to FIGS. 14 and 16, attached to the exterior end cap 256 of the first magnet housing 252 is a pair of diametrically opposed roller guide assemblies 268. A complementary pair of diametrically opposed roller guide assemblies 268 is also attached to the exterior end cap 256 of the second magnet housing 254. Each roller guide assembly 268 includes a housing 270 and a roller bracket 272. Each roller bracket 272 retains an axle 274 with a roller guide 276 mounted on each axle 274.

Referring to FIG. 14, it is seen that one of the roller brackets 272 of each roller guide assembly 268 is securely attached to its housing 270 whereas the roller bracket 272 on the diametrically opposed roller guide assembly 268 is slidable within a guide 278. A pin 280 extends outwardly from each roller bracket 272 and extending between opposing pairs of which are springs 282 to urge the roller brackets toward each other so that the roller guides 276 securely engage the cable 244. The springs 282 allow the magnetic interferometer 246 to be able to accommodate a wide variety of cables having different diameters.

The magnetic interferometer 246 preferably includes a speed and location sensor 284 (FIG. 14) identical to the speed and location sensor 80 of the previously described embodiment, and thus it will not be redescribed here in detail.

Figure 17:
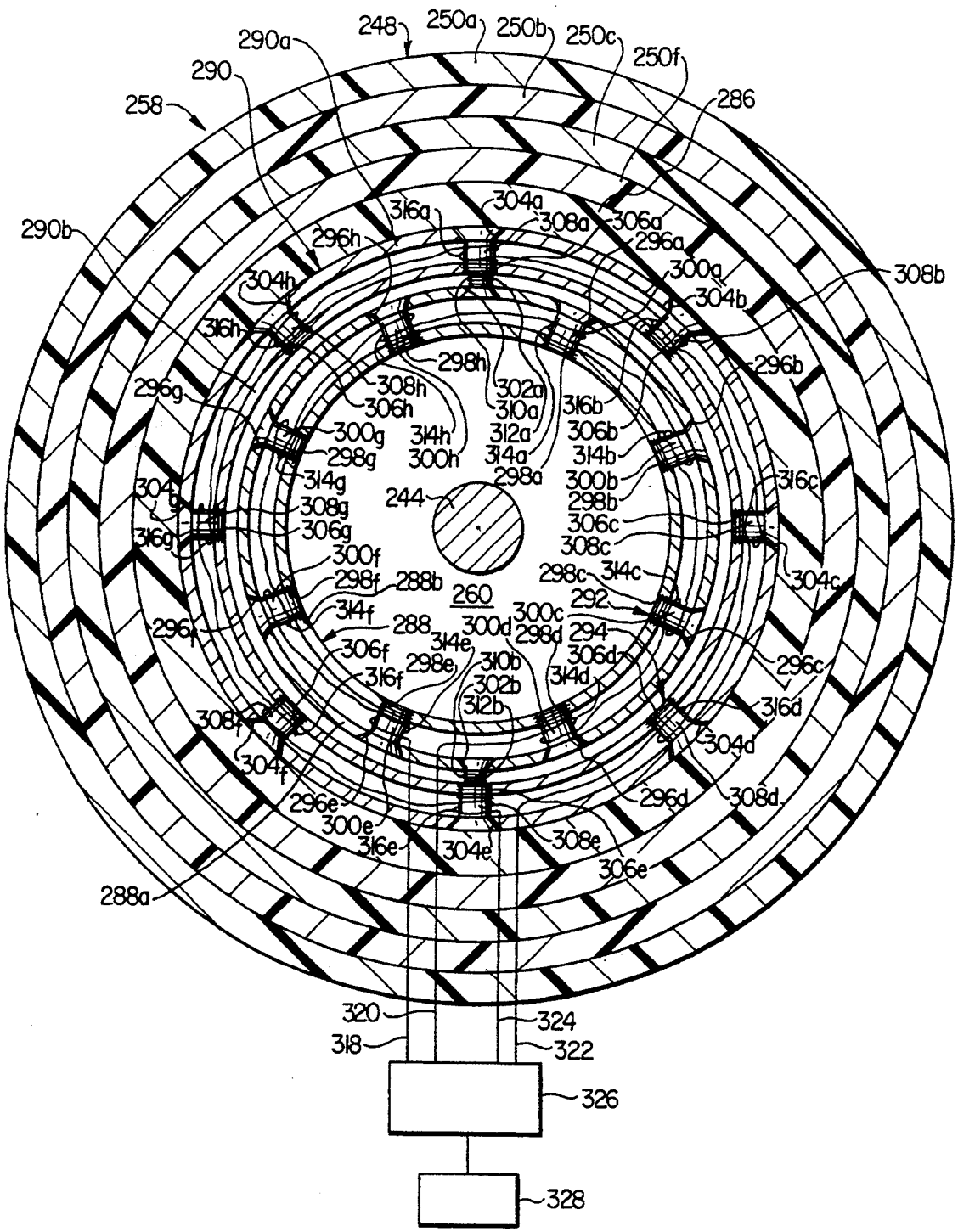
FIG. 17 is a section taken along line 17—17 of FIG. 16.

Referring to FIGS. 16 and 17, the sensing device 258 includes a housing 286, first and second sensor retainers 288 and 290 concentrically disposed within the housing 286, and first and second sensing arrays 292 and 294 retained by the first and second sensor retainers 288 and 290, respectively. The first sensor retainer 288 is disposed within the second sensor retainer 290, and the second sensor retainer 290 is sized to press fit within the housing 286. The housing 286, sized to press fit within the pipe 250f, is constructed of either a magnetically conductive or nonconductive material while the first and second sensor retainers 288 and 290 are constructed of ferrous metal or a similar magnetically conductive material, it being understood that the first and second sensor retainers 288 and 290 are magnetically insulated from one another as is described below.

The first sensor retainer 288 is comprised of a rolled channel iron 288a having an inwardly facing channel and a complementary ring 288b positioned at the perimeter of the channel. The channel iron 288a includes eight symmetrically spaced tapered bores 296a–296h, and the ring 288b includes eight corresponding threaded bores 298a–298h which when aligned with the bores 296a–296h are adapted to threadingly receive eight sensing elements 300a–300h. The channel iron 288a also includes two diametrically opposed tapered bores 302a and 302b, the purpose of which is described below.

Similarly, the second sensor retainer 290 is comprised of a rolled channel iron 290a having an inwardly facing channel and a complementary ring 290b positioned at the perimeter of the channel. The channel iron 290a includes eight symmetrically spaced tapered bores 304a–304h, and the ring 290b includes eight corresponding threaded bores 306a–306h which when aligned with the bores 304a–304h are adapted to threadingly receive eight sensing elements 308a–308h.

TWO of the elements 308a–308h which are diametrically opposed, namely elements 308a and 308e as shown in FIG. 17, have internally threaded bores 310a and 310b, respectively, which when aligned with the bores 302a and 302b are adapted to receive bolts 312a and 312b which rigidly secure the first and second sensor retainers 288 and 290 together. The bolts 312a and 312b are preferably a nonmagnetically conducting material to prevent magnetic flux from flowing between the first and second sensor retainers 288 and 290.

The elements 300a–300h and 308a–308h are configured as rods constructed of a ferromagnetic material and are positioned perpendicular to the axis of and radially spaced around the cable 244 undergoing testing. The ends of the elements 300a–300h and 308a–308h are spaced apart from the cable 244 such that the only direct contact of the magnetic interferometer 246 with the cable 244 is by the roller guides 276.

As shown in FIG. 16, the elements 300a–300h of the first sensing array 292 are aligned in longitudinal planes which are the same for corresponding pairs of the magnets 264 such that they are aligned with the inner half of the magnets 264. The elements 308a–308h of the second sensing array 294 occupy different longitudinal planes than the elements 300a–300h of the first sensing array 292 and are aligned in longitudinal planes which are midway between the longitudinal planes of corresponding pairs of the magnets 264, and the adjacent magnets 264. The elements 308a–308h are positioned within the second sensor retainer 290 such that they are aligned in line with the outer half of the magnets 264.

The elements 300a–300h each have helical wire windings 314a–314h, respectively, which comprise the first sensing array 292. Windings 314a–314h are connected electrically in series and can either be continuously wound or bifilar wound, with bifilar windings resulting in increased amplitudes of the induced voltages.

The elements 308a–308h each have helical wire windings 316a–316h, respectively, which comprise the second sensing array 294. Windings 316a–316h are connected electrically in series and can either be continuously wound or bifilar wound, with bifilar windings resulting in increased amplitudes of the induced voltages.

The first and second sensing arrays 292 and 294 are connected by wires 318, 320 and 322, 324, respectfully, to a digital signal processor 326 and a microcontroller 328, which are identical to the digital signal processor 102 and the microcontroller 104 of the previous embodiment and thus will not be redescribed here in detail.

A Hall effect sensor 330 is also disposed within the magnetic interferometer 246 of the present embodiment as shown in FIG. 16 which functions identically as the Hall effect sensor 112 of the previous embodiment.

In a manner similar to the previously described embodiment, all of the parts of the magnetic interferometer 246 are split in half by means of a medial slit 332, the split halves of which are maintained in facing relationship by a hinge and bracket assembly 334, thereby allowing the magnetic interferometer 246 to be opened and placed around the cable 244 and operated in a manner consistent with the previously described operation of the invention.

While the present invention has been described in detail and with reference to specific examples thereof, it will be apparent to one skilled in the art that various changes and modifications can be made therein without departing from the spirit and scope thereof.

For example, the sensing arrays need not be wired in series as previously described. If more information regarding the nature and location of a defect is required, the individual sensing elements can each be directly wired to the processor. Further, the speed and location of the magnetic interferometer can be determined by the sensing arrays, thereby eliminating the need for the speed and location sensor in one of the roller guides. Specifically, the sensing arrays can be used to detect the lay lines of the cable being tested since they produce deviations in the magnetic flux. Once the number of lay lines per unit length of cable is determined, the speed and location of the magnetic interferometer can be determined by counting the lay lines passed over. In addition, the sensing arrays can be comprised of Hall effect sensors rather than as described. Also, whereas the processor 102 has been described as having a memory 128 separate from its other components, it is understood that the encoded microprocessor 122 has memory which could function as the memory 128.

It should also be noted that although the magnetic interferometer of the present invention has been described in relation to use with metal wire rope or the like, the invention disclosed can be used to find flaws and defects in any material in which such flaws or defects cause perturbations of a magnetic flux passing through the material.

A latitude of modification, change and substitution is intended in the foregoing disclosure and in some instances some features of the invention will be employed without a corresponding use of other features. Accordingly, it is appropriate that the appended claims be construed broadly and in a manner consistent with the scope of the invention.

What is claimed is:

1. Apparatus for magnetically testing an elongate object, comprising:
    a housing having means for receiving said object;
    first and second magnet means disposed in said housing forming a magnetic field therebetween for passing magnetic flux through said object, said first and second magnet means respectively comprising a plurality of circumferentially disposed magnets approximating a cylindrical magnetic coil having a central cavity for receiving said object, wherein said cavities are longitudinally aligned;
    material of low magnetic permeability separating said first and second magnet means such that said magnetic field forms an open magnetic circuit between said first and second magnet means; and
    means for sensing variations in said magnetic flux passing through said object.

2. The apparatus of claim 1 further comprising means for positioning said object centrally within said cavities.

3. The apparatus of claim 2 wherein said positioning means comprises a plurality of roller guides extending between said housing and said object for allowing longitudinal relative movement between said housing and said object.

4. The apparatus of claim 3 further comprising means for determining the distance of said relative movement.

5. The apparatus of claim 4 wherein said determining means comprises a magnetic field detector.

6. The apparatus of claim 5 wherein said sensing means comprises said detector.

7. The apparatus of claim 5 wherein said determining means further comprises a plurality of circumferentially disposed magnets with alternating magnetic poles for producing alternating magnetic fields for detection by said magnetic field detector.

8. The apparatus of claim 7 wherein said magnetic field detector comprises two Hall effect sensors, wherein one Hall effect sensor is for determining the distance of said relative movement and the other Hall effect sensor is for determining the direction of said relative movement.

9. Apparatus for magnetically testing an elongate object, comprising:
    a housing having means for receiving said object;
    first and second magnet means disposed in said housing forming a magnetic field therebetween for passing magnetic flux through said object;
    material of low magnetic permeability separating said first and second magnet means such that said magnetic field forms an open magnetic circuit between said first and second magnet means; and means for sensing variations in said magnetic flux passing through said object comprising first and second circumferentially disposed arrays of sensing elements for receiving said object.

10. The apparatus of claim 9 wherein said first array is disposed closer to said object than said second array to allow said first array to sense different variations in said magnetic flux passing through said object than said second array.

11. The apparatus of claim 9 wherein:

said first and second magnet means respectively comprise a plurality of circumferentially disposed magnets approximating a cylindrical magnetic coil having a central cavity for receiving said object; and said sensing elements of one of said arrays are aligned in longitudinal planes with said magnets of said first and second magnet means.

12. The apparatus of claim 11 wherein said sensing elements of said other array are not aligned in longitudinal planes with said magnets of said first and second magnet means.

13. The apparatus of claim 9 wherein said sensing elements generate electrical signals, and said apparatus further comprises means for processing said signals to quantify the condition of said object.

14. The apparatus of claim 13 further comprising means for filtering said signals prior to said processing to attenuate noise.

15. The apparatus of claim 14 wherein said signals from said first array are filtered at a different center frequency than the signals from said second array.

16. The apparatus of claim 14 wherein said signaling means comprises a band-pass filter with a center frequency of approximately 30 Hz for filtering said signals from one of said arrays and a band-pass filter with a center frequency of approximately 100 Hz for filtering said signals from said other array.

17. The apparatus of claim 13 further comprising means for detecting gradual changes in the cross-sectional area of said object.

18. The apparatus of claim 17 wherein said detecting means generates an electric signal for adjusting said electric signals generated by said sensing elements.

19. The apparatus of claim 13 wherein said detecting means comprises a Hall effect sensor.

20. A method for magnetically testing an elongate object, comprising the steps of:

creating an open magnetic field circuit between first and second magnet means;

passing said object through said magnetic field for passing magnetic flux through said object;

sensing variations in said magnetic flux passing through said object at two separate depths within said object;

generating two separate electric signals from said variations sensed in said sensing step; and processing said signals to determine the integrity of said object.

21. The method of claim 20 further comprising the step of digitizing said signals prior to said processing step.

22. The method of claim 21 further comprising the step of filtering said signals prior to said digitizing step to attenuate noise.

23. The method of claim 20 further comprising the step of filtering said two separate electric signals with different center frequencies.

24. The method of claim 23 further comprising the steps of passing one of said two separate electric signals through a band-pass filter with a center frequency of approximately 30 Hz and passing the other of said two separate electric signals through a band-pass filter with a center frequency of approximately 100 Hz.

25. Apparatus, comprising:

first and second magnet housings each comprising a body with a central cavity;

a plurality of magnets disposed circumferentially within each of said magnet housings to approximate a cylindrical magnetic coil for creating an open magnetic field circuit between said first and second magnet housings;

sensing means for detecting anomalies in said magnetic field and generating corresponding electrical signals;

means for processing said electrical signals; and means for obtaining output from said processed electric signals.

26. The apparatus of claim 25, wherein said magnetic field is circumferentially symmetrical.

27. The apparatus of claim 25 further comprising one or more pairs of diametrically opposed roller guide means connected to each of said magnet housings.

28. The apparatus of claim 25 further comprising means for digitizing said signals prior to said processing to facilitate said processing.

29. The apparatus of claim 28 further comprising means for filtering said signals prior to said digitizing to attenuate noise.

30. The apparatus of claim 25 wherein said sensing means comprises first and second circumferentially disposed arrays of sensing elements.

31. The apparatus of claim 30 wherein said first array circumscribes said second array.

32. The apparatus of claim 30 wherein said sensing elements of said first array are aligned in longitudinal planes with said magnets of said first and second magnet housings.

33. The apparatus of claim 32 wherein said sensing elements of said second array are not aligned in longitudinal planes with said magnets of said first and second magnet housings.

34. The apparatus of claim 30 wherein said signals from said first array are filtered at a different center frequency than the signals from said second array.

35. The apparatus of claim 34 wherein said signaling means comprises a band-pass filter with a center frequency of approximately 30 Hz for filtering said signals from one of said arrays and a band-pass filter with a center frequency of approximately 100 Hz for filtering said signals from said other array.

36. The apparatus of claim 25 further comprising means connected to said housings for storing said electric signals.

37. The apparatus of claim 25 wherein said processing means are connected to said housings.

38. A method for magnetically testing an elongate object, comprising the steps of:

creating an open magnetic field circuit between first and second magnet means;

passing said object through said magnetic field for passing magnetic flux through said object;

generating a first set of electrical signals via a first sensing means disposed a predetermined distance from said object which are responsive to said magnetic flux passing through said object;

generating a second set of electrical signals via a second sensing means disposed a distance from said object not equal to said predetermined distance which are responsive to said magnetic flux passing through said object;

processing said signals to determine the integrity of said object.

39. The method of claim 38 further comprising the step of digitizing said signals prior to said processing step.

40. The method of claim 39 further comprising the step of filtering said signals prior to said digitizing step to attenuate noise.

41. The method of claim 38 further comprising the step of filtering said first and second sets of electric signals with different center frequencies.

42. The method of claim 38 further comprising the steps of passing said first set of electric signals through a band-pass filter with a center frequency of approximately 30 Hz and passing said second set of electric signals through a band-pass filter with a center frequency of approximately 100 Hz.

43. Apparatus for magnetically testing an elongate object, comprising:

means for inducing a magnetic field in a portion of said object such that said magnetic field experiences flux changes according to changes in the condition of said portion;

sensing means for producing electrical signals indicative of said flux changes, said sensing means comprising a housing having a large diameter portion and a reduced-diameter portion, a first array of sensing elements secured to the inner surface of said large-diameter portion, and a second array of sensing elements secured to the inner surface of said reduced-diameter portion, said sensing elements being spaced apart from said object; and means for processing said electrical signals and obtaining output.

44. An apparatus according to claim 43 wherein said sensing elements of said second array are positioned closer to said object than said sensing elements of said first array.

45. An apparatus according to claim 43 wherein said sensing elements of said first and second arrays are aligned in different longitudinal planes, respectively.

46. An apparatus according to claim 43 wherein said sensing elements of said first and second arrays are connected electrically in series, respectively.

47. An apparatus according to claim 43 wherein said inducing means comprises two magnet housings disposed between material of low relative permeability and in proximity to said object such that a magnetic circuit is created by said magnet housings through said object.

48. An apparatus according to claim 43 wherein said sensing elements comprise ferromagnetic rods wound with a helical wire.

49. An apparatus according to claim 48 wherein said ferromagnetic rod is positioned perpendicular to said object.

50. An apparatus according to claim 48 wherein said wire winding is bifilar.

51. Apparatus for magnetically testing an elongate object moving relative to said apparatus, comprising:

means for inducing a magnetic field in a portion of said object whereby said magnetic field experiences flux changes according to changes in the condition of said portion, said means for inducing a magnetic field comprising first and second magnet housings and a plurality of permanent magnets spaced circumferentially within each of said magnet housings, each of said magnet housings defining a central cavity for receiving said object;

sensing means disposed between said first and second magnet housings for producing electrical signals indicative of said flux changes, said sensing means comprising:

a housing defining a central cavity for receiving said object; and first and second arrays having a plurality of sensing elements supported in said housing in a perpendicular spaced relationship from said object, comprising a conductive rod and a helical wire winding, respectively, said sensing elements arranged circumferentially around said portion of said cable such that said sensing elements of said first array are positioned closer to said object than the sensing elements of said second array, said sensing elements of each of said arrays being electrically connected in series; and means for supporting said object for relative movement with respect to said inducing means and said sensing means.

52. An apparatus according to claim 51 wherein said sensing elements of said first array are aligned in the same longitudinal planes as corresponding ones of said permanent magnets.

53. An apparatus according to claim 51 wherein said sensing elements of said second array are aligned in longitudinal planes between corresponding ones of said permanent magnets.

54. An apparatus according to claim 51 further comprising means for processing said electrical signals.

* * * * *

UNITED STATES PATENT AND TRADEMARK OFFICE
CERTIFICATE OF CORRECTION

PATENT NO. : 5,402,066
DATED : March 28, 1995
INVENTOR(S) : William Hickman, Jr. et al.

It is certified that error appears in the above-indentified patent and that said Letters Patent is hereby corrected as shown below:

On the title page, column 1, line 1
The Title, "G31102 AND APPARATUS FOR MAGNETICALLY TESTING ELONGATE OBJECTS USING TWO CIRCUMFERENTIALLY DISPOSED ARRAYS OF MAGNETS AND TWO CIRCUMFERENTIALLY DISPOSED ARRAYS OF SENSORS"

should be -- METHOD AND APPARATUS FOR MAGNETICALLY TESTING ELONGATE OBJECTS --.

Signed and Sealed this

Third Day of October, 1995

Attest:

BRUCE LEHMAN

Attesting Officer    Commissioner of Patents and Trademarks